(12) United States Patent
Erdmann et al.

(10) Patent No.: US 11,734,269 B2
(45) Date of Patent: Aug. 22, 2023

(54) SYSTEMS, METHODS, AND STORAGE MEDIA USEFUL IN A COMPUTER HEALTHCARE SYSTEM TO CONSUME CLINICAL QUALITY LANGUAGE QUERIES IN A PROGRAMMATIC MANNER

(71) Applicant: CERNER INNOVATION, INC., Kansas City, KS (US)

(72) Inventors: Cole Erdmann, Kansas City, MO (US); Joseph Marcus Overhage, Zionsville, IN (US); Bharat Sutariya, Parkville, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 267 days.

(21) Appl. No.: 17/136,778

(22) Filed: Dec. 29, 2020

(65) Prior Publication Data

US 2021/0200766 A1    Jul. 1, 2021

Related U.S. Application Data

(60) Provisional application No. 62/955,808, filed on Dec. 31, 2019.

(51) Int. Cl.
| | | |
|---|---|---|
| *G16H 20/40* | (2018.01) | |
| *G06F 16/2453* | (2019.01) | |
| *G06F 16/248* | (2019.01) | |
| *G16H 70/20* | (2018.01) | |
| *G16H 30/20* | (2018.01) | |
| *G16H 40/20* | (2018.01) | |
| *G16H 50/70* | (2018.01) | |

(52) U.S. Cl.
CPC ...... *G06F 16/24534* (2019.01); *G06F 16/248* (2019.01); *G16H 30/20* (2018.01); *G16H 40/20* (2018.01); *G16H 50/70* (2018.01); *G16H 70/20* (2018.01)

(58) Field of Classification Search
CPC ............ G06F 16/24534; G06F 16/248; G06F 16/2433; G16H 30/20; G16H 40/20; G16H 50/70; G16H 70/20; G16H 10/60
See application file for complete search history.

(56) References Cited

U.S. PATENT DOCUMENTS

| | | | |
|---|---|---|---|
| 2017/0006135 A1* | 1/2017 | Siebel | G06Q 10/06 |
| 2019/0073403 A1* | 3/2019 | Fusari | G06F 16/2457 |
| 2019/0095478 A1* | 3/2019 | Tankersley | G06F 11/3476 |

\* cited by examiner

*Primary Examiner* — Jason S Tiedeman
*Assistant Examiner* — Liza Tony Kanaan
(74) *Attorney, Agent, or Firm* — Invoke

(57) ABSTRACT

Systems, methods, and storage media useful in a computer healthcare system to consume clinical quality language queries in a programmatic manner are disclosed. Exemplary implementations may: load a CQL query from a third party; transform the CQL query to a modified structured query language query; load medical data elements from a database record store for each patient in one or more defined patient populations; execute the modified SQL query on medical data elements from the database record store for each patient in one or more defined patient populations; and load results of the modified SQL query.

17 Claims, 7 Drawing Sheets

Task  Edit  View  Patient  Chart  Links  Application Loading  Options  Current  Add  Help 🏠 Home | ▼ | Links | ▼ | ⁞ ⁞ 📄 New Sticky Note | 🗔 View Sticky Notes | 📎 Tear Off | 📎 Attach | ⊘ Charges | ℬ Charge Entry Thayer, Ethyl Louise ☒

👤 Thayer, Ethyl Louise      DOB: 02/18/1940      Age: 77 years
                              Weight: 130 lbs.     MRN: 00300079

< > ▼ | 🏠 Patient Summary

🗛 ▢ ▢ ▢ 🔍 🖉 | 100% | ▼ | ○ ○ ↻

Ambulatory Workflow | Inpatient Workflow | Discharge Workflow | Quick Bill

Menu

Recommendations
Clinical Indicators
Documents
Labs
Vital Signs
Interdisciplinary Team
Care Pathways
Problems
Assessment and Plan Create Note
Select Note Labs ⊿ Primary Labs                           OCT 24, 2017
Glucose POC
K
Creatinine         ACE Inhibitor References
BNP
Vital Signs    Rationale:
Temp               CQL 2019 - CDC
°C                 CQL 2020 - INDUSTRY
BP
mmHg
RR
bpm

SYSTEMS, METHODS, AND STORAGE MEDIA USEFUL IN A COMPUTER HEALTHCARE SYSTEM TO CONSUME CLINICAL QUALITY LANGUAGE QUERIES IN A PROGRAMMATIC MANNER

CROSS-REFERENCE TO RELATED APPLICATIONS

This application claims the benefit of U.S. Provisional Application No. 62/955,808, filed on Dec. 31, 2019, and entitled "Systems, Methods, and Storage Media Useful In A Computer Healthcare System To Consume Clinical Quality Language Queries in a Programmatic Manner," the entirety of all of which is incorporated by reference herein.

BACKGROUND

The US health care system is made of multiple hospital systems, including private and government funded hospital systems. Private hospital systems are owned by an organization other than the government or state. Private hospital systems can be not for profit, for profit or a hybrid. Government funded hospital systems are funded by local, state and/or federal funds. In some instances, a hospital system may receive both private and public funding.

Examples of private hospital systems currently include HCA Healthcare, Ascension Heath, Intermountain Healthcare, and Mayo Clinic Health System. Example of public hospital systems currently include NYC Health & Hospitals, TMC University Health, Department of Defense and Veterans Affairs.

Previous solutions are unable to integrate third party queries across multiple hospital systems and are time consuming and expensive. It takes weeks if not months to perform third party queries on large populations of patients. Integrating third party information to cover multiple hospital systems and thousands to millions of patients is time consuming and prone to error.

SUMMARY

The dynamic system and methods depicting provide analytic capability that brings scale to processing third-party queries in a programmatic manner. The system and method consumes clinical quality language (CQL) queries in a programmatic manner. The system sits on top of a collection of client EHR databases (such as Cerner HealtheIntent) the system and method processes third-party queries by leveraging the meta data stored inside FHIR resource produced by CQL 108 or other knowledge resource and distribute and automate the completion of activities to manage a patient's health and care.

The system and method provide insights within a healthcare system, across the country and across the world. This scale allows setting of industry benchmarks to identify health systems performing above or below targets across venues of care. The system and method provides the ability to push the insights generated by the process analyzer system and method into the front-end of user applications. The process analyzer system and method ability to identify opportunities to improve compliance and to guide clinical best practice to create a direct link between data insights and practitioners directly impacting patient care.

One aspect of the present disclosure relates to a system configured useful in a computer healthcare system to consume clinical quality language queries in a programmatic manner. The system may include one or more hardware processors configured by machine-readable instructions. The processor(s) may be configured to load a CQL query from a third party. The processor(s) may be configured to transform the CQL query to a modified structured query language query. The processor(s) may be configured to load medical data elements from a database record store for each patient in one or more defined patient populations. The processor(s) may be configured to execute the modified SQL query on medical data elements from the database record store for each patient in one or more defined patient populations. The processor(s) may be configured to load results of the modified SQL query. The system and method of the present invention allows for third-party queries to be executed across multiple hospital systems in an efficient and cost effective manner. Queries that may have previously taken weeks or months, can now be complied within hours or minutes. The system and methods of the present invention allows Integrating third party information and queries to be applied to millions of patients across multiple hospital systems.

Clinical Quality Language (CQL) provides the ability to express logic that is human readable yet structured enough for processing a query electronically across EHR systems. CQL utilizes an HL7 standard authoring language that is a core component in the effort to harmonize standards used for electronic clinical quality measures (eCQMs) and clinical decision support (CDS). CQL queries may originate with the government and government agencies, such as the Centers for Disease Control and Prevention, Centers for Medicare and Medicaid Services, Agency for Healthcare Research and Quality. CQL queries also may originate from the private healthcare Gain efficiencies in software development lifecycle The system and method of the present invention does not require manual translation to recode logic for CQL queries and reduces the time and cost for development of measures and clinical care pathways. The system and method of the present invention is EHR agnostic and can utilize data from multiple EHR providers and vendors.

The system and method of the present invention eliminates variability across institutions (such as hospital systems and employers who provide healthcare) and allows multiple institutions to assess compliances against standard measures and care protocols provided by CQL queries from third parties. Thus, the multiple institutions have more accurate and meaningful benchmarking.

The system and method of the present invention allows the engagement subject matter experts by processing CQL queries in a programmatic manner for large populations of patients. This reducing the burden on institutions to translate clinical logic and CQL queries themselves. The system and methods of the present invention allows the ability to author and edit logic as need to influence healthcare program and standard requirements as needed. The system and method of the present t invention provides scalable concepts and calculations used across various platforms, institutions and use cases.

In some implementations of the system, transforming the CQL query to a modified SQL query may include parsing the CQL query into define, function and operator constructs.

In some implementations of the system, the processor(s) may be configured to consume a model-info.xml file while parsing the CQL query for informing the structure of the modified SQL query. In some implementations of the system, the structure may be fast healthcare interoperability resources.

In some implementations of the system, CQL may be an hl7 standard authoring language that is a core component in the effort to harmonize standards used for electronic clinical quality measures and clinical decision support.

In some implementations of the system, the CQL may provide the ability to express logic that is human readable yet structured enough for processing a query electronically across electronic health record systems.

In some implementations of the system, the results of the modified SQL query may be patients in the one or more defined patient populations who satisfy the medical data elements of the CQL query.

In some implementations of the system, the CQL query may provide criteria for clinical healthcare guidelines.

Another aspect of the present disclosure relates to a method useful in a computer healthcare system to consume clinical quality language queries in a programmatic manner. The method may include loading a CQL query from a third party. The method may include transforming the CQL query to a modified structured query language query. The method may include loading medical data elements from a database record store for each patient in one or more defined patient populations. The method may include executing the modified SQL query on medical data elements from the database record store for each patient in one or more defined patient populations. The method may include loading results of the modified SQL query.

Yet another aspect of the present disclosure relates to a non-transient computer-readable storage medium having instructions embodied thereon, the instructions being executable by one or more processors to perform a method useful in a computer healthcare system to consume clinical quality language queries in a programmatic manner. The method may include loading a CQL query from a third party. The method may include transforming the CQL query to a modified structured query language query. The method may include loading medical data elements from a database record store for each patient in one or more defined patient populations. The method may include executing the modified SQL query on medical data elements from the database record store for each patient in one or more defined patient populations. The method may include loading results of the modified SQL query.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

FIGS. 3A and 3B illustrate a display of alerting that a patient has satisfied the criteria for a CQL query received from a third party.

DETAILED DESCRIPTION

Figure 1A:
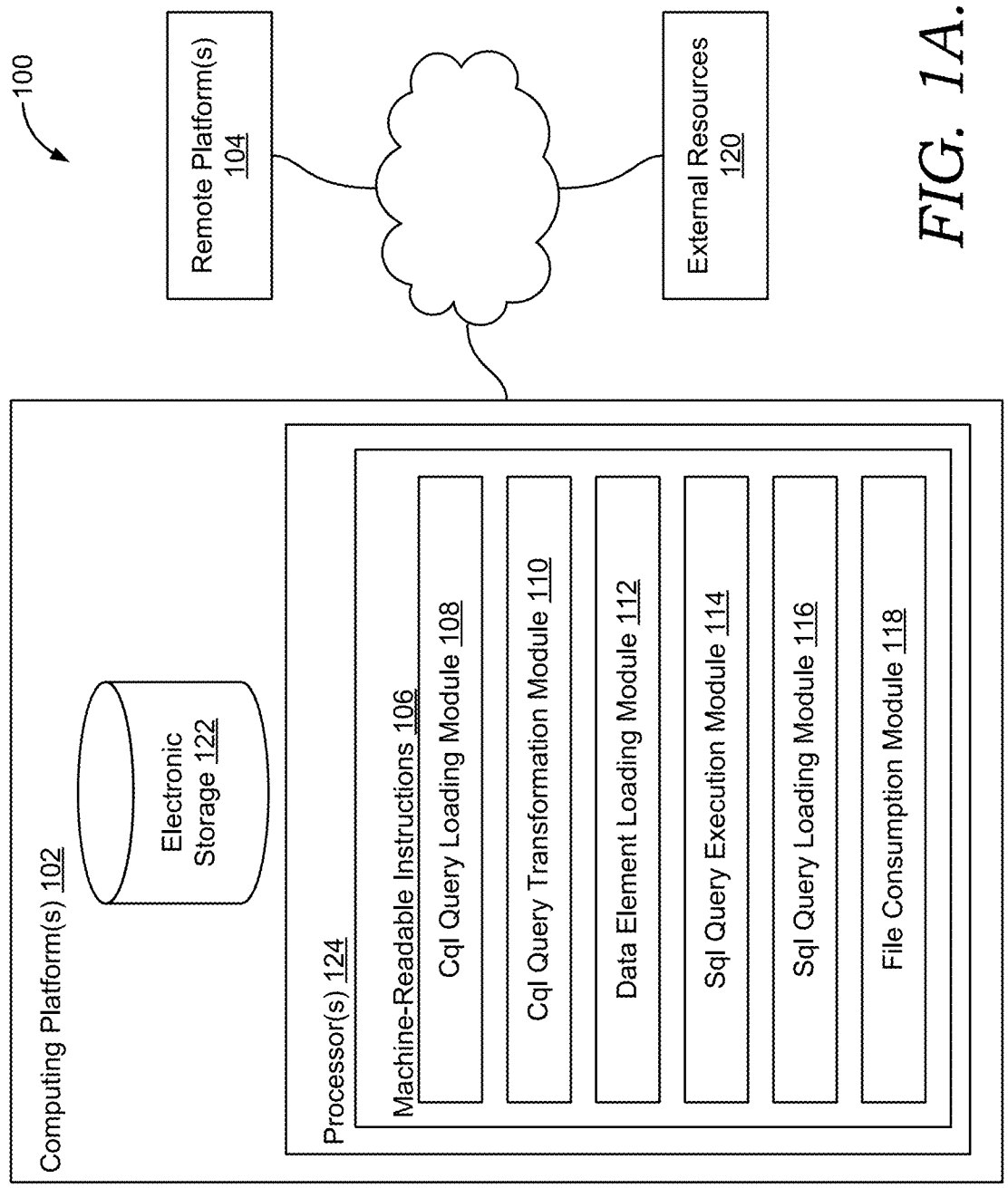
FIGS. 1A and 1B illustrates a system configured useful in a computer healthcare system to consume clinical quality language queries in a programmatic manner, in accordance with one or more implementations.
Figure 1B:
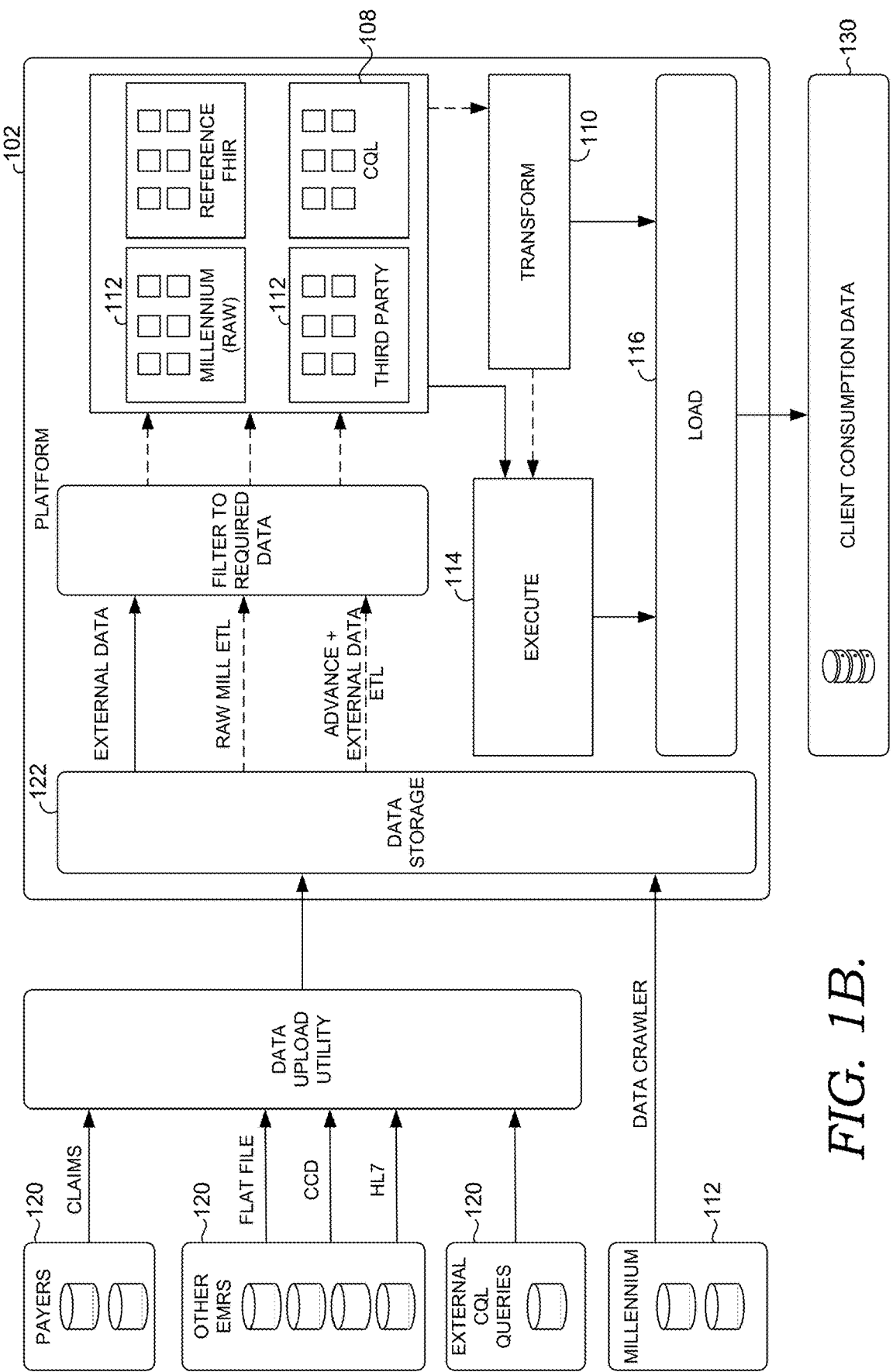

FIGS. 1A and 1B illustrates a system 100 configured useful in a computer healthcare system to consume clinical quality language queries in a programmatic manner, in accordance with one or more implementations. In some implementations, system 100 may include one or more computing platforms 102. Computing platform(s) 102 may be configured to communicate with one or more remote platforms 104 according to a client/server architecture, a peer-to-peer architecture, and/or other architectures. Remote platform(s) 104 may be configured to communicate with other remote platforms via computing platform(s) 102 and/ or according to a client/server architecture, a peer-to-peer architecture, and/or other architectures. Users may access system 100 via remote platform(s) 104.

In some implementations, computing platform(s) 102, remote platform(s) 104, and/or external resources 120 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 102, remote platform(s) 104, and/or external resources 120 may be operatively linked via some other communication media.

A given remote platform 104 may include one or more processors configured to execute computer program modules. The computer program modules may be configured to enable an expert or user associated with the given remote platform 104 to interface with system 100 and/or external resources 120, and/or provide other functionality attributed herein to remote platform(s) 104. By way of non-limiting example, a given remote platform 104 and/or a given computing platform 102 may include one or more of a server, a desktop computer, a laptop computer, a handheld computer, a tablet computing platform, a NetBook, a Smartphone, a gaming console, and/or other computing platforms.

External resources 120 may include sources of information outside of system 100, external entities participating with system 100, and/or other resources. In some implementations, some or all of the functionality attributed herein to external resources 120 may be provided by resources included in system 100.

Computing platform(s) 102 may include electronic storage 122, one or more processors 124, and/or other components. Computing platform(s) 102 may include communication lines, or ports to enable the exchange of information with a network and/or other computing platforms. Illustration of computing platform(s) 102 in FIG. 1 is not intended to be limiting. Computing platform(s) 102 may include a plurality of hardware, software, and/or firmware components operating together to provide the functionality attributed herein to computing platform(s) 102. For example, computing platform(s) 102 may be implemented by a cloud of computing platforms operating together as computing platform(s) 102.

Electronic storage 122 may comprise non-transitory storage media that electronically stores information. The electronic storage media of electronic storage 122 may include one or both of system storage that is provided integrally (i.e., substantially non-removable) with computing platform(s) 102 and/or removable storage that is removably connectable to computing platform(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from computing platform(s) 102, information received from remote platform(s) 104, and/or other information that enables computing platform(s) 102 to function as described herein.

Processor(s) 124 may be configured to provide information processing capabilities in computing platform(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device, or processor(s) 124 may represent processing functionality of a plurality of devices operating in coordination. Processor(s) 124 may be configured to execute modules 108, 110, 112, 114, 116, and/or 118, and/or other modules. Processor(s) 124 may be configured to execute modules 108, 110, 112, 114, 116, and/or 118, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 108, 110, 112, 114, 116, and/or 118 are illustrated in FIG. 1 as being implemented within a single processing unit, in implementations in which processor(s) 124 includes multiple processing units, one or more of modules 108, 110, 112, 114, 116, and/or 118 may be implemented remotely from the other modules. The description of the functionality provided by the different modules 108, 110, 112, 114, 116, and/or 118 described below is for illustrative purposes, and is not intended to be limiting, as any of modules 108, 110, 112, 114, 116, and/or 118 may provide more or less functionality than is described. For example, one or more of modules 108, 110, 112, 114, 116, and/or 118 may be eliminated, and some or all of its functionality may be provided by other ones of modules 108, 110, 112, 114, 116, and/or 118. As another example, processor(s) 124 may be configured to execute one or more additional modules that may perform some or all of the functionality attributed below to one of modules 108, 110, 112, 114, 116, and/or 118.

Computing platform(s) 102 may be configured by machine-readable instructions 106. Machine-readable instructions 106 may include one or more instruction modules. The instruction modules may include computer program modules. The instruction modules may include one or more of CQL query loading module 108, CQL query transformation module 110, data element loading module 112, SQL query execution module 114, SQL query loading module 116, file consumption module 118, and/or other instruction modules.

Platform 102 may be Cerner HealthIntent as shown in FIG. 1B. Platform 102 can ingest third-party clinical content/knowledge at scale to support an interoperable clinical knowledge management ecosystem. Platform 102 delivers knowledge-based products such as quality measures, clinical pathways and consumer engagement by integrating third-party intelligence into care delivery processes. Platform 102 comprises information from multiple EHR databases, such as multiple hospital systems.

CQL query loading module 108 may be configured to load a CQL query from a third party. By way of non-limiting example, transforming the CQL query to a modified SQL query. "Functions" in CQL come in perhaps three forms (or "constructs"), preceded by the keywords "define" and "function" and then as well as with a library of operators defined as helpers in the language.

The "define" construct is an expression of CQL code bound to a name which can be referenced throughout the library. This expression takes no arguments, and when called, returns its result as a value.

The "function" construct is an expression of CQL code bound to a name that additionally takes any number of declared, typed arguments. Like the "define", it can be referenced by name, provided its arguments, and evaluated by efficiently processing CQL queries against large volumes of patient data.

CQL includes a core library of operator constructs. These operator constructs are applied against data types defined in CQL and FHIR, and are composed together to create the larger "define" and "function" expressions. CQL includes around 150 operators that can be used to compose a CQL query (and to compose the various "define" and "function" constructs that make up a query).

Platform 102 executes standard authoring language Clinical Quality Language (CQL) on FHIR projections of patient health records and longitudinal records. This allows CQL processing to fit within platform 102 and utilization of channels for third-party information.

CQL query transformation module 110 may be configured to transform the CQL query to a modified structured SQL query.

Data element loading module 112 may be configured to load medical data elements from a database record store 122 for each patient in one or more defined patient populations. Medical data elements include any data input or including in patient(s) into the patient(s) electronic health record (EHR). Medical data elements may include patient condition, orders, patient demographic information (age, gender, height, weight), vital signs, test results, images, medications, medication administration, tasks, facility information and caregiver information. The database record store may include medical data elements from multiple hospital systems. The database record store 122 includes medical data elements from a variety of electronic health records such medical data elements directly from Cerner Millennium and transferred data from external resources 120 such as other vendor electronic health records, (flat files, CCD and HL7 610 and the like) as shown in FIG. 1B. The medical data elements from a variety of hospital systems and EHRs is stored in data record store 122. In some embodiments, the medical data elements are de-identified.

SQL query execution module 114 may be configured to execute the modified SQL query on medical data elements from the database record store for each patient in one or more defined patient populations. The one or more defined patient populations typically include over 10000 patients. The patients may be from a single hospital system or multiple hospital system. Parallel processing may be used to execute the modified SQL query.

SQL query loading module 116 may be configured to load results of the modified SQL query. The results of the modified SQL query may be patients in the one or more defined patient populations who satisfy the medical data elements of the CQL query. Data element extraction module 112 may be configured to extract medical data elements for the healthcare process from the database record store 122 for each of the patients in one or more defined patient populations. The database record store 122 may include medical data elements from multiple hospital systems. The database record store 122 includes medical data elements from a variety of electronic health records such medical data elements directly from Cerner Millennium and transferred data from external resources 120 such as other vendor electronic health records, (flat files, CCD and HL7 610 and the like) as shown in FIG. 1B. The medical data elements from a variety of hospital systems and EHRs is stored in data record store 122.

File consumption module 118 may be configured to consume a model-info.xml file while parsing the CQL query for informing the structure of the modified SQL query. The structure may be fast healthcare interoperability resources (FHIR).

CQL is defined to operate over different FHIR data models/versions. It does this by consuming a special model-info.xml file during parsing of the CQL code to the Expression Logical Model (ELM) intermediate form. This model-info file informs the CQL parser what structure of data a query will be given. Several different of these model-info files include model-info files for QUICK (the native CQL data model), model-info files for sFHIR, and model-info files for the various FHIR versions.

In one embodiment, model-info.xml file for FHIR version 3.0.0 is utilized. A library of helpers (a library of "function" constructs) of FHIRHelpers is used during parsing of FHIR version 3.0.0-compliant queries. CQL queries are parsed to FHIR version 3.0.0 model-info.xml file, and to the FHIRHelpers.CQL library. When they validate queries to give us, they need to be validated against those standard files, otherwise we'll be forced to make alterations to the CQL files by hand which will bar us from easily consuming them in a programmatic manner.

In some implementations, CQL is a standard authoring language that is core component in the effort to harmonize standards used for electronic clinical quality measures and clinical decision support. In some implementations, the CQL may provide the ability to express logic that is human readable yet structured enough for processing a query electronically across electronic health record systems. In some implementations, the CQL query may provide criteria for clinical healthcare guidelines. In some implementations, the clinical healthcare guidelines may include criteria for patients who qualify for one or more vaccinations. In some implementations, the clinical healthcare guidelines may include criteria for patients who qualify for opioid intervention. The clinical healthcare guidelines may include guidelines related to any variety of healthcare issues.

Results from applying CQL criteria to a defined population may be loaded to a to distributed file system such as data store 130 across clients or multiple hospital systems such as a cross client process data store. The data can be utilized for data aggregation, benchmarking, ad-hoc analysis and additional obfuscation by clients and/or hospital systems.

Figure 4:
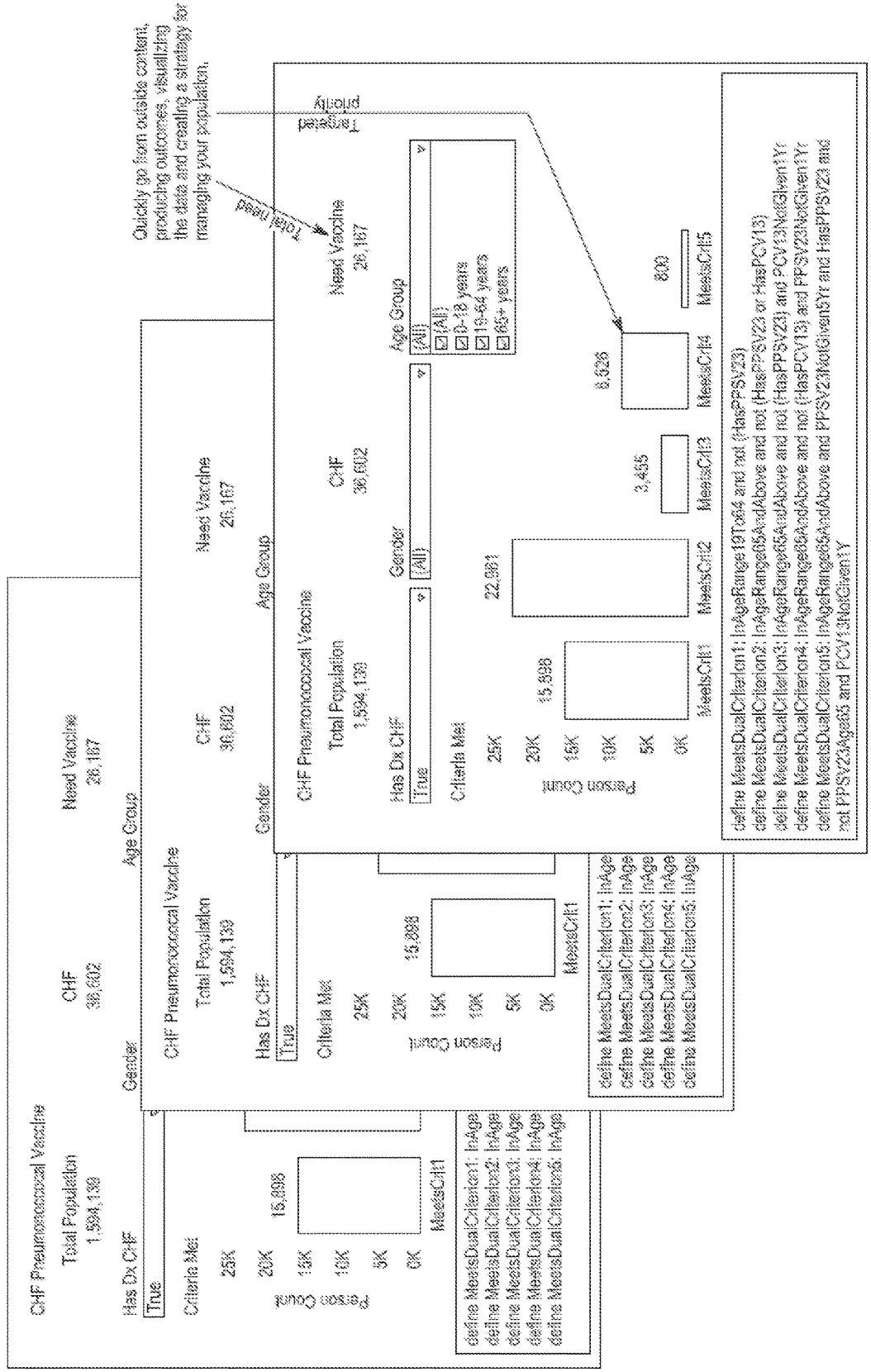
FIG. 4 illustrates data regarding a population that satisfies criteria for a CQL query received from a third party.

The clients and/or hospital systems can consume the aggregated, obfuscated data loaded into the data store 130. For example, with reference to FIG. 4, displays patients out of a total defined population that satisfy CQL queries for being at risk for heart disease or needing a vaccine. Thus, a strategy can be created for managing populations of patient is based on satisfaction of CQL queries.

Figure 3B:
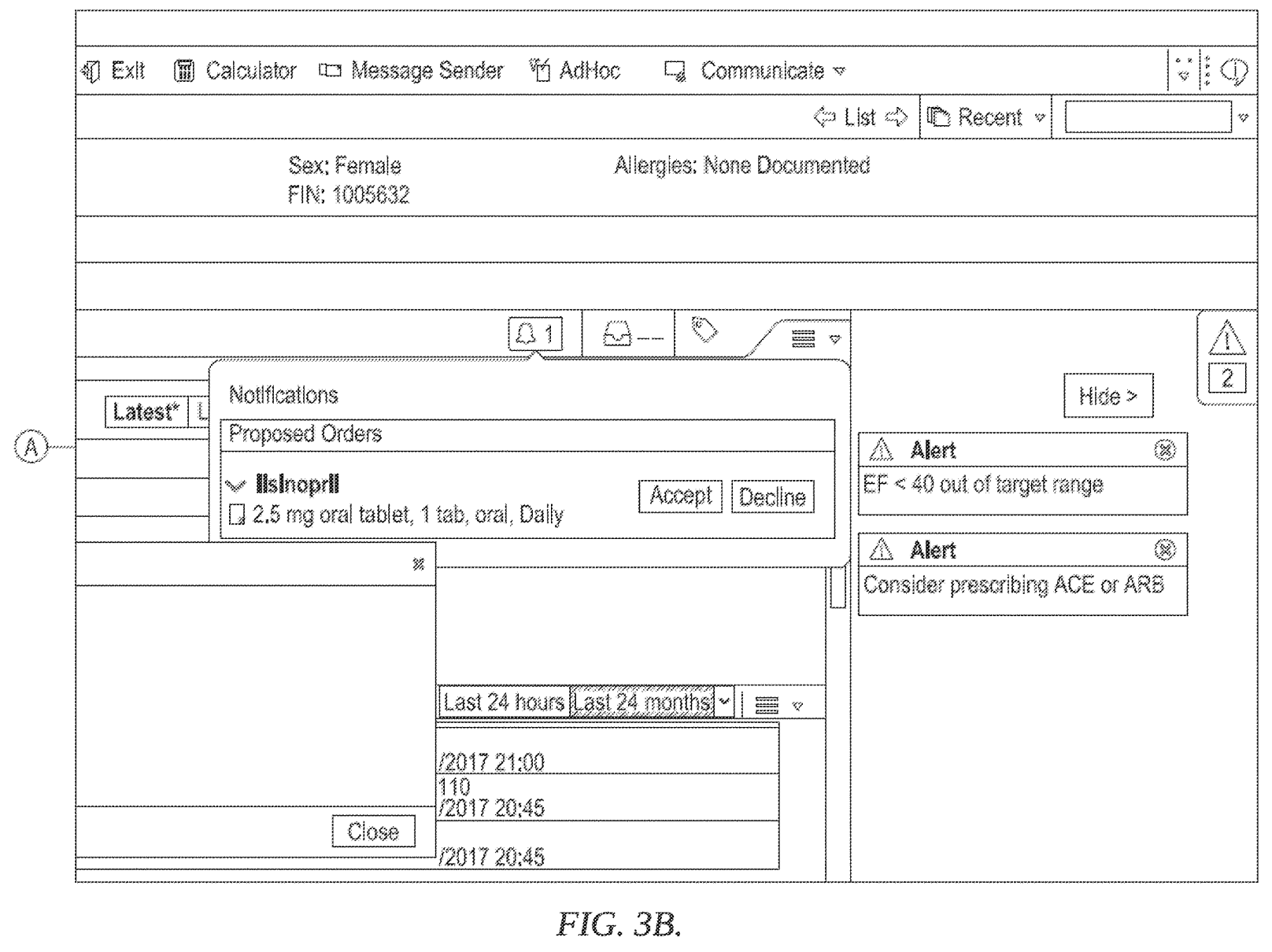

In addition, with reference to FIGS. 3A and 3B, one or more alerts may be provided based on a single patient satisfying one or more CQL queries(s). For example, based on criteria received in a CQL query in 2019 from the CDC and a CQL query received from an industry partner, the patient in FIGS. 3A and 3B has lab tests out of range and should be considered for an ACE inhibitor.

In some implementations, the CQL query may be compiled as a modified SQL query without using a separate CQL compiler.

Figure 2A:
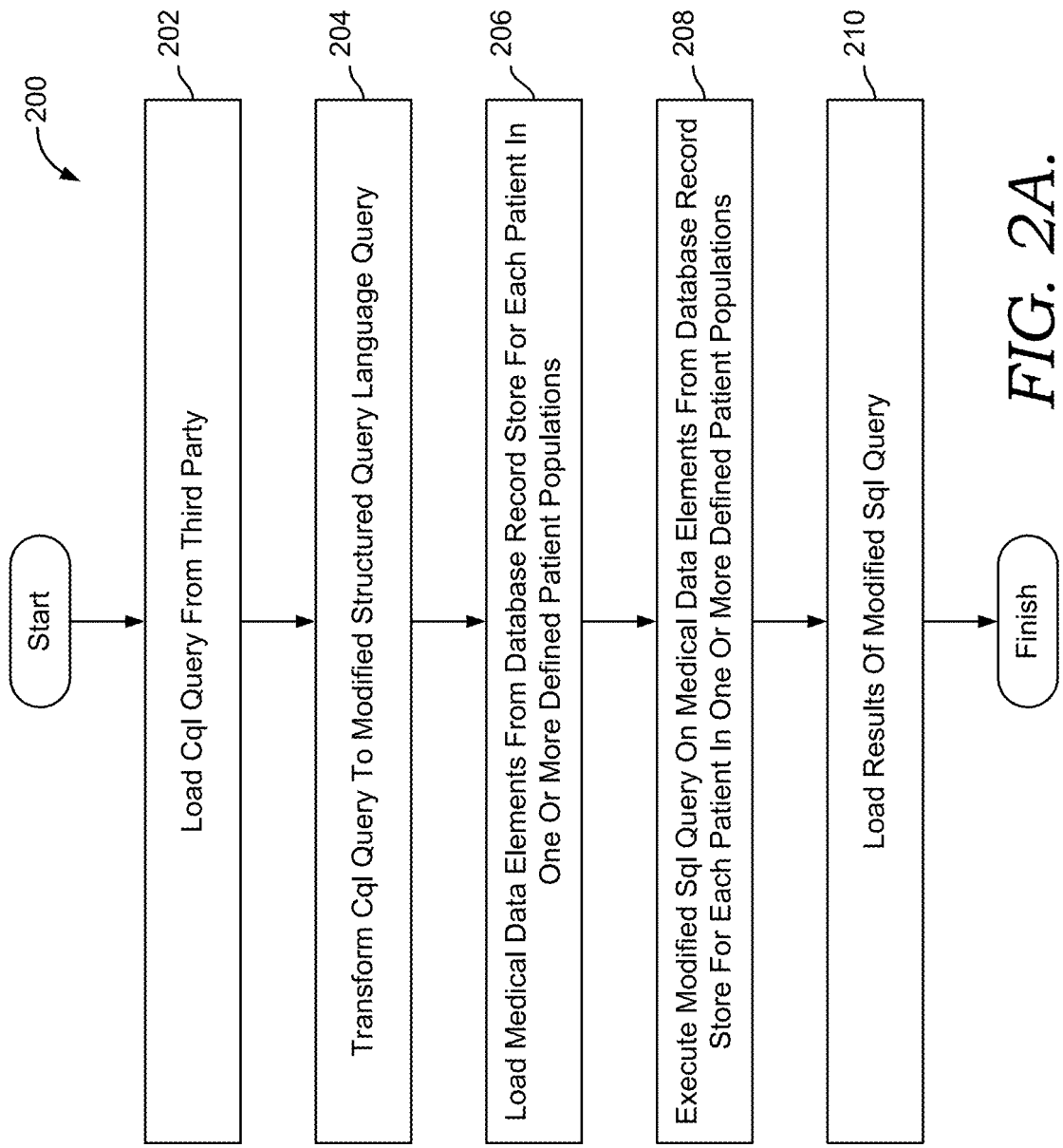
FIGS. 2A and/or 2B illustrates a method useful in a computer healthcare system to consume clinical quality language queries in a programmatic manner, in accordance with one or more implementations.

FIGS. 2A and/or 2B illustrates a method 200 useful in a computer healthcare system to consume clinical quality language queries in a programmatic manner, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIGS. 2A and/or 2B and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

FIG. 2A illustrates method 200, in accordance with one or more implementations.

An operation 202 may include loading a CQL query from a third party. Operation 202 may be performed by one or more hardware processors configured by machine-readable instructions including a module that is the same as or similar to CQL query loading module 108, in accordance with one or more implementations.

An operation 204 may include transforming the CQL query to a modified structured query language query. Operation 204 may be performed by one or more hardware processors configured by machine-readable instructions including a module that is the same as or similar to CQL query transformation module 110, in accordance with one or more implementations.

An operation 206 may include loading medical data elements from a database record store for each patient in one or more defined patient populations. Operation 206 may be performed by one or more hardware processors configured by machine-readable instructions including a module that is the same as or similar to data element loading module 112, in accordance with one or more implementations.

An operation 208 may include executing the modified SQL query on medical data elements from the database record store for each patient in one or more defined patient populations. Operation 208 may be performed by one or more hardware processors configured by machine-readable instructions including a module that is the same as or similar to SQL query execution module 114, in accordance with one or more implementations.

An operation 210 may include loading results of the modified SQL query. Operation 210 may be performed by one or more hardware processors configured by machine-readable instructions including a module that is the same as or similar to SQL query loading module 116, in accordance with one or more implementations.

Figure 2B:
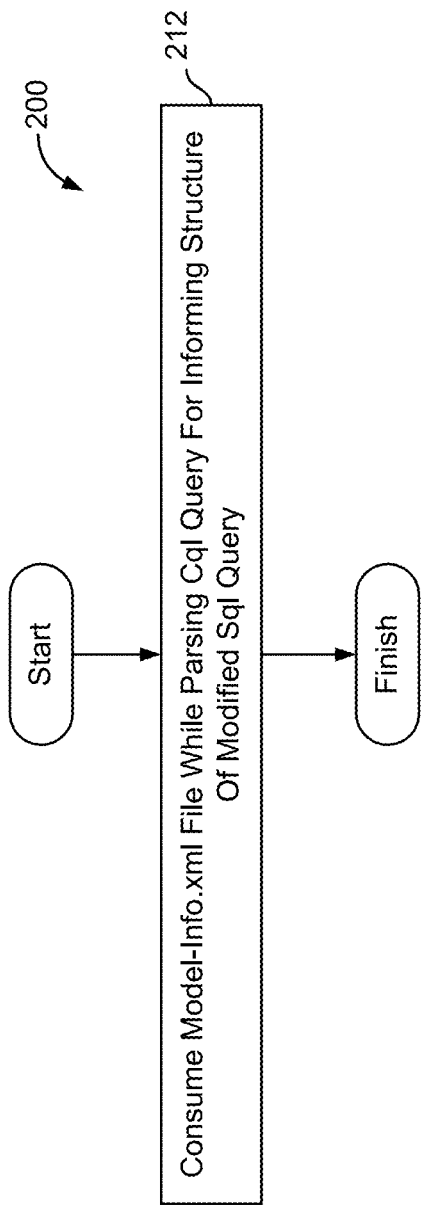

FIG. 2B illustrates method 200, in accordance with one or more implementations.

An operation 212 may include consuming a model-info.xml file while parsing the CQL query for informing the structure of the modified SQL query. The structure may be fast healthcare interoperability resources. Operation 212 may be performed by one or more hardware processors configured by machine-readable instructions including a module that is the same as or similar to file consumption module 118, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to consume clinical quality language (CQL) queries in a programmatic manner, the system comprising:
   one or more hardware processors configured by machine-readable instructions to:
      load a CQL query from a third party;
      transform the CQL query to a modified structured query language (SQL) query in a programmatic manner at least by:
         consuming an Extensible Markup Language (XML) file that indicates a structure of data in the CQL query comprising Define, Function, and Operator constructs;
         based on the structure of data in the CQL query as indicated by the XML file, validating and parsing the CQL query into an intermediate Expression Logical Model (ELM) form; and
         generating the modified SQL query from the intermediate ELM form;
      load medical data elements from a database record store for each patient in one or more defined patient populations;
      execute the modified SQL query on medical data elements from the database record store for each patient in one or more defined patient populations; and
      load results of the modified SQL query.

2. The system of claim 1, wherein a structure of the modified SQL query is fast healthcare interoperability resources.

3. The system of claim 1, wherein CQL is an hl7 standard authoring language that is a core component in an effort to harmonize standards used for electronic clinical quality measures and clinical decision support.

4. The system of claim 1, wherein the CQL provides an ability to express logic that is human readable yet structured enough for processing a query electronically across electronic health record systems.

5. The system of claim 1, wherein the results of the modified SQL query are patients in the one or more defined patient populations who satisfy the medical data elements of the CQL query.

6. The system of claim 1, wherein the CQL query provides criteria for clinical healthcare guidelines.

7. A dynamic method useful in a computer healthcare system to consume clinical quality language (CQL) queries in a programmatic manner, the method comprising:
   loading a CQL query from a third party;
      transforming the CQL query to a modified structured query language (SQL) query in a programmatic manner at least by:
         consuming an Extensible Markup Language (XML) file that indicates a structure of data in the CQL query comprising Define, Function, and Operator constructs;
         based on the structure of data in the CQL query as indicated by the XML file, validating and parsing the CQL query into an intermediate Expression Logical Model (ELM) form;
         generating the modified SQL query from the intermediate ELM form;
   loading medical data elements from a database record store for each patient in one or more defined patient populations;
   executing the modified SQL query on medical data elements from the database record store for each patient in one or more defined patient populations; and
   loading results of the modified SQL query.

8. The method of claim 7 wherein a structure of the modified SQL query is fast healthcare interoperability resources.

9. The method of claim 7, wherein CQL is an hl7 standard authoring language that is a core component in the effort to harmonize standards used for electronic clinical quality measures and clinical decision support.

10. The method of claim 7, wherein the CQL provides the ability to express logic that is human readable yet structured enough for processing a query electronically across electronic health record systems.

11. The method of claim 7, wherein the results of the modified SQL query are patients in the one or more defined patient populations who satisfy the medical data elements of the CQL query.

12. The method of claim 7, wherein the CQL query provides criteria for clinical healthcare guidelines.

13. A non-transitory computer-readable storage medium having instructions embodied thereon, the instructions being executable by one or more processors to perform a method useful in a computer healthcare system to consume clinical quality language (CQL) queries in a programmatic manner, the method comprising:
- loading a CQL query from a third party;
- transforming the CQL query to a modified structured query language (SQL) query in a programmatic manner at least by:
  - consuming an Extensible Markup Language (XML) file that indicates a structure of data in the CQL query comprising Define, Function, and Operator constructs;
  - based on the structure of data in the CQL query as indicated by the XML file, validating and parsing the CQL query into an intermediate Expression Logical Model (ELM) form; and
  - generating the modified SQL query from the intermediate ELM form;
- loading medical data elements from a database record store for each patient in one or more defined patient populations;
- executing the modified SQL query on medical data elements from the database record store for each patient in one or more defined patient populations; and
- loading results of the modified SQL query.

14. The computer-readable storage medium of claim 13, wherein a structure of the modified SQL query is fast healthcare interoperability resources.

15. The computer-readable storage medium of claim 13, wherein CQL is an hl7 standard authoring language that is a core component in an effort to harmonize standards used for electronic clinical quality measures and clinical decision support.

16. The computer-readable storage medium of claim 13, wherein the CQL provides the ability to express logic that is human readable yet structured enough for processing a query electronically across electronic health record systems.

17. The computer-readable storage medium of claim 13, wherein the results of the modified SQL query are patients in the one or more defined patient populations who satisfy the medical data elements of the CQL query.

* * * * *